United States Patent
Kobayashi et al.

(10) Patent No.: US 8,216,831 B2
(45) Date of Patent: Jul. 10, 2012

(54) CELL CULTURE DEVICE

(75) Inventors: Toyoshige Kobayashi, Fujimino (JP); Kazutoshi Kan, Kawagoe (JP)

(73) Assignee: Hitachi, Ltd., Tokyo (JP)

( * ) Notice: Subject to any disclaimer, the term of this patent is extended or adjusted under 35 U.S.C. 154(b) by 173 days.

(21) Appl. No.: 12/292,725

(22) Filed: Nov. 25, 2008

(65) Prior Publication Data

US 2009/0137026 A1    May 28, 2009

(30) Foreign Application Priority Data

Nov. 27, 2007 (JP) ................. 2007-305237

(51) Int. Cl.
- C12M 3/00 (2006.01)
- C12M 1/36 (2006.01)
- C12M 1/22 (2006.01)
- C12M 1/00 (2006.01)

(52) U.S. Cl. ............... 435/305.2; 435/286.4; 435/289.1; 435/294.1

(58) Field of Classification Search ............. 435/305.2, 435/286.4, 289.1, 294.1
See application file for complete search history.

(56) References Cited

U.S. PATENT DOCUMENTS

| | | | | |
|---|---|---|---|---|
| 4,012,288 A * | 3/1977 | Lyman et al. | ............ | 435/305.2 |
| 4,937,194 A | 6/1990 | Pattillo et al. | | |
| 6,653,124 B1 * | 11/2003 | Freeman | ............ | 435/297.1 |
| 7,270,996 B2 * | 9/2007 | Cannon et al. | ............ | 435/293.1 |
| 2006/0019375 A1 * | 1/2006 | Seidl et al. | ............ | 435/289.1 |
| 2006/0115893 A1 | 6/2006 | Kobayashi et al. | | |
| 2007/0148764 A1 | 6/2007 | Suzuki et al. | | |
| 2007/0281351 A1 | 12/2007 | Kobayashi et al. | | |
| 2008/0057568 A1 | 3/2008 | Kan et al. | | |
| 2008/0145924 A1 | 6/2008 | Kobayashi et al. | | |

FOREIGN PATENT DOCUMENTS

| | | |
|---|---|---|
| JP | 63-503201 | 5/1987 |
| JP | 01-225476 | 9/1989 |
| JP | 2006-149237 | 11/2004 |
| JP | 2005-287466 | 10/2005 |
| JP | 2006-149237 | 6/2006 |
| WO | WO 2005/059091 A1 | 12/2004 |

OTHER PUBLICATIONS

Office Action from Japanese Patent Office for corresponding Japanese Patent Application No. JP-2007-305237, dated Sep. 29, 2009, in Japanese with partial English translation.
Japanese Patent Office Notice of Rejection for JP-2009-271519, dated Feb. 15, 2011, in Japanese (3 pages) with partial English translation (2 pages) with verified statement of translation.

* cited by examiner

*Primary Examiner* — Nathan Bowers
*Assistant Examiner* — Gautam Prakash
(74) *Attorney, Agent, or Firm* — Stites & Harbison, PLLC; Juan Carlos A. Marquez, Esq.

(57) ABSTRACT

A cell culture device comprises a fluid mechanism for branching a liquid appropriately in its flow passage when the liquid is injected to a plurality of culture vessels in a set and feeding equal amounts of the culture broth to the culture vessels at the same time. The device, in one form, has one or plural recess portions so that one or plural culture vessels can be contained in alignment, in view of space efficiency, m x n (row x column) pieces of culture vessels can be set in a matrix type. By using a pump, the culture broth is branched by a multi-way valve for distributing the liquid in an appropriate amount from a tank containing the culture broth, and the liquid is fed at the same time to the plurality of culture vessels in the culture vessel set.

6 Claims, 11 Drawing Sheets

CELL CULTURE DEVICE

CLAIM OF PRIORITY

The present application claims priority from Japanese patent application JP 2007-305237 filed on Nov. 27, 2007, the content of which is hereby incorporated by reference into this application.

BACKGROUND OF THE INVENTION

1. Field of the Invention

The present invention relates to a cell culture device for culturing a cell using a culture vessel.

2. Background Art

Cell culture work has been carried out by a skilled worker in a clean room which is sterilized as much as possible. Thus, if a cell is to be cultured in a large quantity for industrial application, there is a possibility that a burden on the workers is increased, time and costs are required for education/training of the workers, and human errors and mix-up of test substances and moreover, those carrying bacteria might cause contamination and the like, which requires much cost to cope with them. That makes a huge barrier in industrial application. Thus, by automating a series of culture work, those problems can be solved.

Regarding the automation of processes in the cell culture, an example of automation of a process to input a culture broth into a culture vessel such as cell seeding and medium replacement is described in Patent Document 1. In patent Document 1, by attaching/detaching a culture vessel and a joint on a manipulator side by a robot manipulator, a method of connecting the joint and the culture vessel is realized. At that time, leakage of culture broth from a tube of the joint and inside the culture vessel is prevented by a valve made of a resin film so that the connection can be made while a clean state is maintained. Also, the culture broth is supplied from beneath and discharged from above for broth replacement while the culture vessel connected by the manipulator stood in a vertical direction.

Also, a method for transferring a predetermined amount of a culture broth to a plurality of culture vessels more efficiently is proposed and its example is described in Patent Document 2. In this method, means for connecting a culture vessel and a flow passage by an aseptic connector, controlling communication of the broth by a three-way valve, and feeding the broth to the plurality of culture vessels branched in the flow passage is provided.

Patent Document 1: JP Patent Publication (Kokai) No. 2006-149237

Patent Document 2: JP Patent Publication (Kohyo) No. 63-503201

SUMMARY OF THE INVENTION

As methods of transplantation, there are methods of auto-transplantation in which a cell collected from himself/herself is in vitro treated and returned to himself/herself and allo-transplantation in which a cell collected from another person such as a donor body is in vitro treated for homotransplantations. In the auto-transplantation, since it is only necessary to create a necessary and sufficient amount of tissues for treating an affected portion of himself/herself and an amount of the cell that can be collected is small, culture is conducted using one or plural culture vessels. On the other hand, in the allo-transplantation, many cells provided from a donor body and the like are used and the number of cells is largely increased so as to produce numerous tissues, many culture vessels are used for culture.

Thus, if the culture vessels are treated one by one in processes of cell seeding or medium replacement of automatic culture for the allo-transplantation, a lot of time is required, which causes problems not only in the cost aspect but also non-uniform activation of the cells and medium and other environmental stresses might act on the cells and incur trouble in quality control. Thus, in order to reduce treatment time for the cell seeding and medium replacement, a method for feeding an equal amount of a culture broth to a plurality of culture vessels at the same time is required.

The present invention was made in view of such circumstances, and a fluid mechanism is provided that a plurality of culture vessels can be detachably attached to a flow passage at once, a broth is appropriately branched in the flow passage, and an equal amount of the culture broth is fed to the plurality of culture vessels.

In order to solve the above problems, the present invention provides the following means:

A culture vessel set that has one or plural recess portions in which one or plural culture vessels can be aligned and housed is provided. In the culture vessel set, m×n (row×column) pieces of culture vessels can be set in a matrix state in view of efficiency of space utilization. In the culture vessel set, spring-type fixtures are installed in a depth direction and a width direction, respectively, and the culture vessel side face is pressed by these two spring-type fixtures to be fixed to the culture vessel set and also made detachable. The culture vessel is configured to have a hole for supplying/discharging a culture broth from its upper face to/from the inside, and a manipulator having a joint for connecting the flow passage to the hole in the culture vessel is provided.

In the passage for feeding the broth, first, a cell is inputted from a cell input mechanism in an airlock structure, and cell concentration is adjusted in a tank. At that time, a process of cell input is removed in medium replacement. Using a pump, a cell suspension liquid is separated by a multi-way valve at the tank and fed to the culture vessel in the culture vessel set. At that time, at an outlet of the multi-way valve, n pieces of blocks having m pieces of outlets with an equal height in the horizontal direction are prepared for a single electromagnetic valve, and the liquid is put into the culture vessels at the equal height in the horizontal direction at the same time by the unit of block by ON/OFF of the electromagnetic valve. At that time, the electromagnetic valve in the outlet direction is controlled by a sensor on the outlet side so that an equal amount of medium feeding can be made, and the object can be realized.

That is, the cell culture device according to the present invention is provided with a liquid vessel for containing a liquid, a culture vessel set for holding a plurality of culture vessels provided with a liquid introduction port and a liquid exit port, respectively, liquid introduction/discharge means for introducing the liquid contained in the liquid vessel to the liquid introduction ports of the plurality of culture vessels held by the culture vessel set an discharging the liquid from the liquid exit ports of the culture vessels, a connecting member for connecting the plurality of liquid introduction ports and the plurality of liquid exit ports to the liquid introduction/discharge means, and state changing means for changing the culture vessel set from a horizontal state to a vertical state with its center line as a rotating axis when the liquid introduction/discharge means is operated. And when the culture vessel set is in the vertical state, the plurality of liquid exit ports and the plurality of liquid introduction ports are arranged with an interval between them in a perpendicular direction.

Here, the culture vessel set can hold m×n pieces (m is an integer of 2 or more, n is an integer of 1 or more) of culture vessels, and when the culture vessel set is in the vertical state, in m pieces of the culture vessels on the k-th stage (k is an integer of $1 \leqq k \leqq n$), a pressure of liquid feed by the liquid introduction/discharge means is the same at the plurality of liquid introduction ports, respectively.

The above-mentioned cell culture device is further provided with switch means for switching the liquid feed operation by the liquid introduction/discharge means to the plurality of culture vessels for m pieces of the culture vessels on the k-th stage. It may be so configured that a sensor for detecting discharge of the liquid from the exit port of m pieces of the culture vessels to which the liquid has been introduced by the liquid introduction/discharge means is provided, and when the sensor detects discharge of the liquid, the switch means switches the operation of the liquid introduction/discharge means so that the liquid is fed to m pieces of the culture vessels on the subsequent stage.

Also, the cell culture device according to the present invention is provided with a liquid vessel for containing a liquid, a culture vessel set for holding a plurality of culture vessels provided with a liquid introduction port and a liquid exit port, respectively, liquid introduction/discharge means for introducing the liquid contained in the liquid vessel to the liquid introduction ports of the plurality of culture vessels held by the culture vessel set and discharging the liquid from the plurality of liquid exit ports of the culture vessels, a connecting member for connecting the plurality of liquid introduction ports and the plurality of liquid exit ports to the liquid introduction/discharge means, and state changing means for changing the culture vessel set from a horizontal state to a vertical state when the liquid introduction/discharge means is operated. And when the culture vessel set is in the vertical state, the liquid introduction/discharge means feeds the liquid to the plurality of culture vessels located at the same height at the same time.

Also, the plurality of culture vessels are classified into a plurality of culture vessel groups to each of which the liquid is fed at the same time. In this case, the cell culture device is provided with switch means for switching the culture vessel group so that the liquid introduction means sequentially feeds the liquid to the plurality of culture vessel groups at the same time according to the switching operation by the switch means.

Additional features of the present invention will be made apparent from the best mode for carrying out the invention and the attached drawings.

According to the present invention, a plurality of culture vessels can be detachably attached to a flow passage at the same time, the liquid is branched appropriately by the flow passage, and an equal amount of a culture broth can be fed to the plurality of culture vessels. Thus, a cell can be cultured efficiently.

DESCRIPTION OF SYMBOLS 1 cell culture device
10 culture vessel
11 culture space
12 connection hole
121 liquid injection port
122 liquid discharge port
13 culture vessel side face
14 culture chamber
15 culture broth with cell
16 air-lock chamber
161 outer door
162 inner door
163 flow-passage manipulator
17 pump
18 culture broth container
181 culture broth (for dilution)
19 tank
191 liquid level sensor
192 diluted culture broth with cell
20 culture vessel set
21 recess portion
22 spring-type fixture
23 removal hole
24 waste container
25 used culture broth (waste)
30 joint
31 flow passage
32 manipulator
33 rotating shaft
34 joint arm
35 motor
36 vertical direction
37 rotating direction
38 stopper
39 base
301 arm
302 motor 303 rotating shaft
304 connection groove
305 sensor
306 sensor
40 multi-way valve
41 electromagnetic valve
42 tube
43 connector
44 manifold
401 electromagnetic valve
402 electromagnetic valve
403 electromagnetic valve
411 spring
412 plug
413 flow passage
414 solenoid
415 electric wire
416 permanent magnet
417 diaphragm

DETAILED DESCRIPTION OF THE PREFERRED EMBODIMENTS

A preferred embodiment of the present invention will be described below referring to the attached drawings. However, attention should be paid that the present embodiment is only an example to realize the present invention and does not limit a technical scope of the present invention. In each drawing, the same reference numerals are given to common configuration.

<Configuration of Cell Culture Device>

Figure 1:
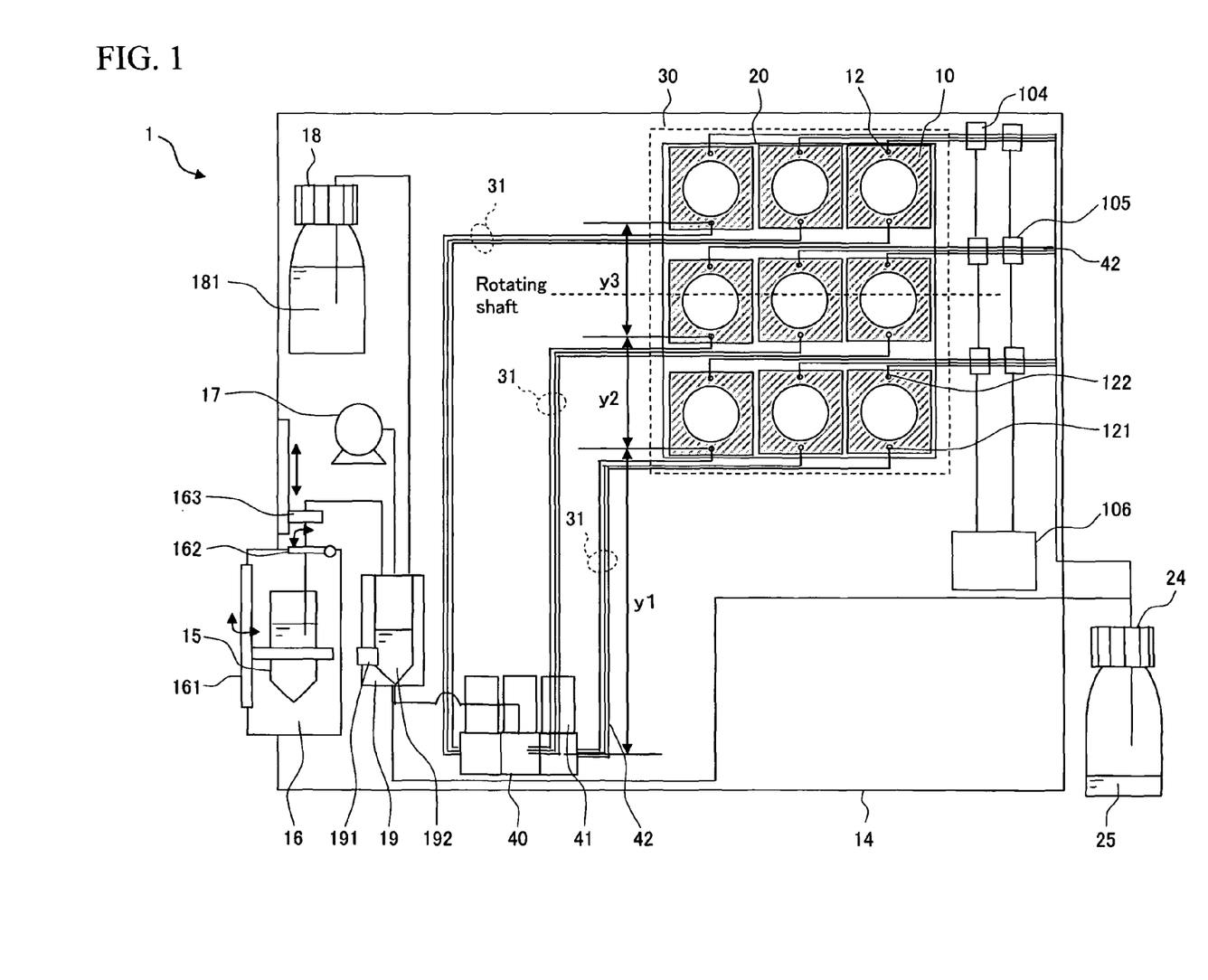
FIG. 1 is a diagram illustrating outline configuration of a cell culture device according to an embodiment of the present invention.

FIG. 1 is a diagram illustrating outline configuration of a cell culture device 1 according to an embodiment of the present invention and particularly illustrates an entire liquid-feeding system inside a culture chamber 14 for injecting a liquid into a plurality of culture vessels 10.

The cell culture device 1 is provided with the culture chamber 14, an air-lock chamber 16 for input of a culture broth 15 with cell into the culture chamber 14, and a waste container 24 for recovering a waste 25. The air-lock chamber 16 is provided with an outer door 161 and an inner door 162 so that inside of the culture chamber 14 is not contaminated when the culture broth 15 with cell is inputted. Also, the cell culture device 1 is provided with, in the culture chamber 14, a culture vessel set 20 for containing a plurality of culture vessels 10, a joint 30 for injecting and discharging the culture broth 15 or a washing liquid with respect to each of the culture vessels 10, a multi-way valve 40 for switching a flow of the culture broth 15, a flow passage 31 (constituted by a plurality of tubes 42) provided between the joint 30 and the multi-way valve 40, a culture broth container 18 for containing a culture broth 181 for dilution, a tank 19 connected to the air-lock chamber 16 and the culture broth container 18 and for diluting the culture broth 15 with cell, a pump 17 for moving the culture broth 15 with cell to the tank 19, a liquid level sensor 104 for sensing a liquid coming from a waste port of the culture vessel 10, an electromagnetic valve 105 for closing the tube 42, and a controller 106 for controlling the electromagnetic valve 105 according to a sensing result by the liquid level sensor 104.

<Configuration of Culture Vessel and Culture Vessel Set>

Figure 2:
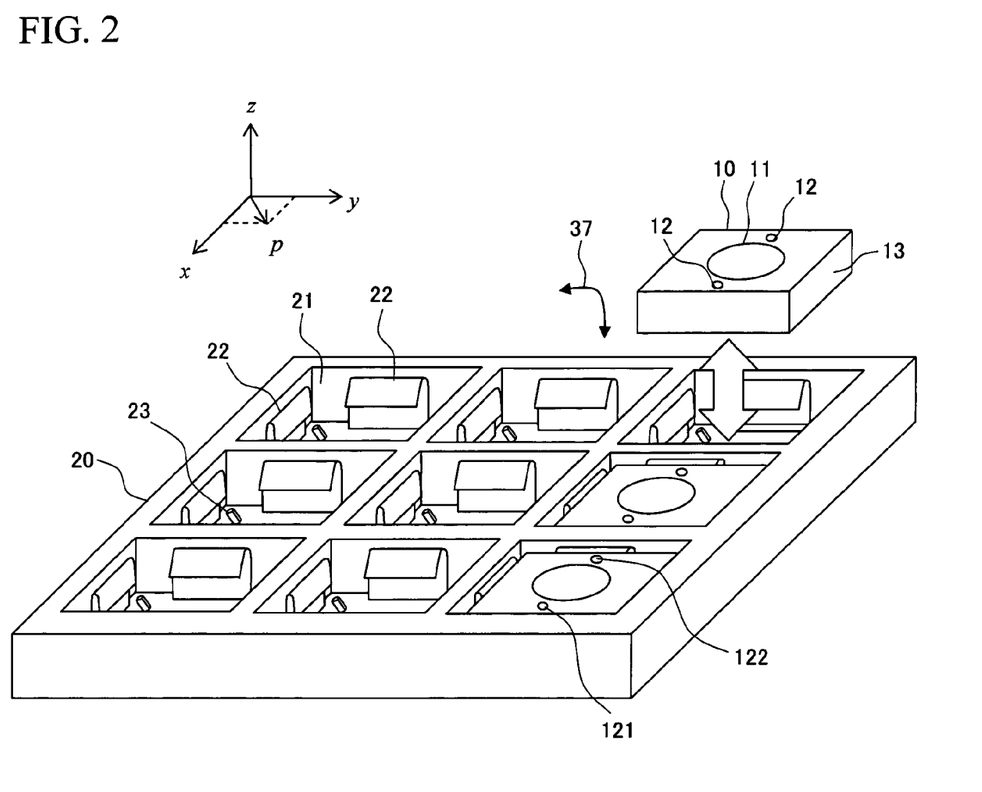
FIG. 2 is a diagram illustrating outline configuration of a culture vessel set that has one or plural recess portions inside and can fix the culture vessel by two spring-type fixtures.

FIG. 2 is an outline diagram illustrating connection between the culture vessel 10 and the culture vessel set 20 according to this embodiment.

As shown in FIG. 2, the culture vessel set 20 has one or plural recess portions 21, in which the culture vessel 10 is set. At that time, each culture vessel 10 is fixed in the recess portion 21 by pressing a culture vessel side face 13 in a P direction (See FIG. 2) using two spring-type fixtures 22 in the recess portions 21. The spring-type fixtures 22 are fixed to a bottom face or a side face of the recess portion 21 in the culture vessel set 20. Also, the spring-type fixtures 22 are installed in the perpendicular direction to each other and use a material having strength such as stainless so that the fixture does not rust in a high-humidity environment during culture. When the culture vessel 10 is set in the recess portion 21, the spring-type fixtures 22 press the culture vessel side faces 13 in the two directions (synthesized into a force in the P direction) so that a positional accuracy in a horizontal direction of the culture vessel 10 when the culture vessel 10 is set can be improved. Moreover, the force is applied on the whole culture vessel side faces 13 by that, movement in the perpendicular direction when an external force is applied or removal of the culture vessel 10 from the culture vessel set 20 can be prevented. For removal of the culture vessel 10, a removal hole 23 provided at the culture vessel set 20 is used.

The culture vessel 10 has a culture space 11 for culturing cell in an internal closed system, in which a culture broth is placed and a cell is cultured. The culture vessel 10 has a pair of connection holes 12 for injection and discharge of the culture broth inside from the outside on an upper face portion of the culture vessel 10. When the culture broth is injected, the culture broth is injected from one of the connection holes 12 (injection port), and liquid or air is discharged from the other connection hole 12 (discharge port). Since the culture vessel 10 has the connection holes 12 on the upper face portion, the culture vessels 10 set in the culture vessel set 20 all have the connection holes 12 arranged on the upper face portion of the culture vessel set 20. Thus, by connecting the joint 30 connected to the flow passage 31 and the upper face portion of the culture vessel set 20, the flow passage 31 and the culture vessels 10 can be connected to each other.

The culture vessel set 20 connected to the joint 30 is stood upright by a manipulator 32 from the horizontal direction to the perpendicular direction, the culture broth and the like is introduced from the connection hole (liquid injection port) located below of the two connection holes 12 and the liquid is injected. Thus, each culture vessel 10 is installed in the culture vessel set 20 so that injection of a diluted culture broth 192 into a liquid injection port 121, which is the lower connection hole 12 of the culture vessel 10 and liquid or air discharge of a used culture broth 25 from a liquid discharge port 122, which is the upper connection hole 12 of the culture vessel 10 can be carried out when all the culture vessels 10 installed in the culture vessel set 20 are stood upright. As mentioned above, by injecting the diluted culture broth 192 from below (liquid injection port) and discharging the used culture broth 25 or air from above (liquid discharge port), air bubbles having entered inside the culture space 11 are eliminated or the used culture broth 25 is discharged efficiently from above (liquid discharge port), and the uniformly diluted culture broth 192 can be injected into the culture space 11.

<Connection Between Joint and Culture Vessel Set>

FIGS. 3A to 3D are outline diagrams illustrating an operation relating to the connection between the joint 30 and the culture vessel set 20, and using them the configuration of the manipulator 32 having the joint 30 for injecting liquid into the culture vessel 10 in the culture vessel set 20 and a series of operations of the connection between the culture vessel set 20 and the joint 30 by the manipulator will be described.

Figure 3A:
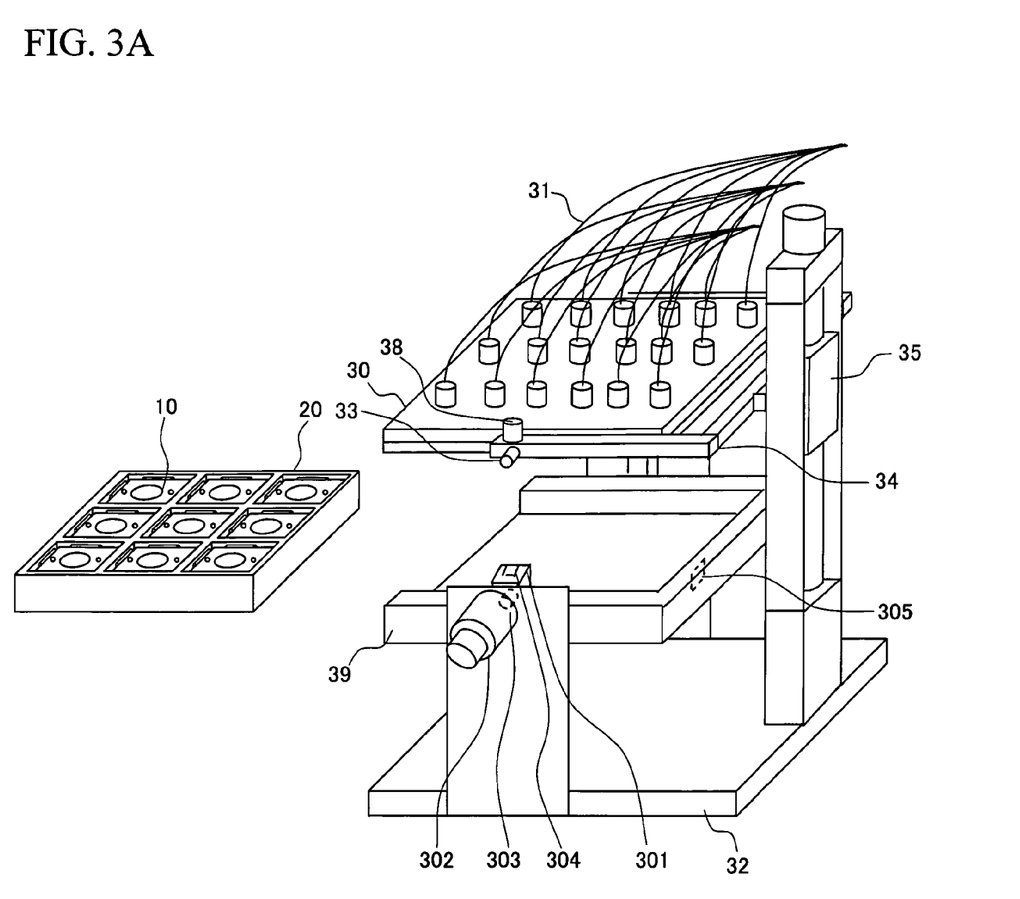
FIG. 3A is a conceptual diagram (1) relating to connection between a joint connected to a flow passage and the culture vessel set.

FIG. 3A shows a state before the connection. First, configuration of each element will be described. The joint 30 is connected to the manipulator 32 by a rotating shaft 33 and a joint arm 34. The joint arm 34 is moved vertically (in an arrow 36 direction) by a motor 35 of the manipulator 32, and the joint 30 can be moved vertically (in the arrow 36 direction) with that motion. The joint 30 can be rotated from the horizontal direction to the perpendicular direction (in an arrow 37 direction) with the rotating shaft 33 as its axis. A stopper 38 is provided so that the joint 30 is not freely rotated at this time and the rotating shaft 33 can be locked and fixed at a predetermined position. A base 39 of the culture vessel set 20 is connected to an arm 301. The arm 301 has a rotating shaft 303 connected to a motor 302. Moreover, at the arm 301, a connection groove 304 is provided so that the rotating shaft 303 and the rotating shaft 33 of the joint 30 are overlapped on the same line.

Figure 3B:
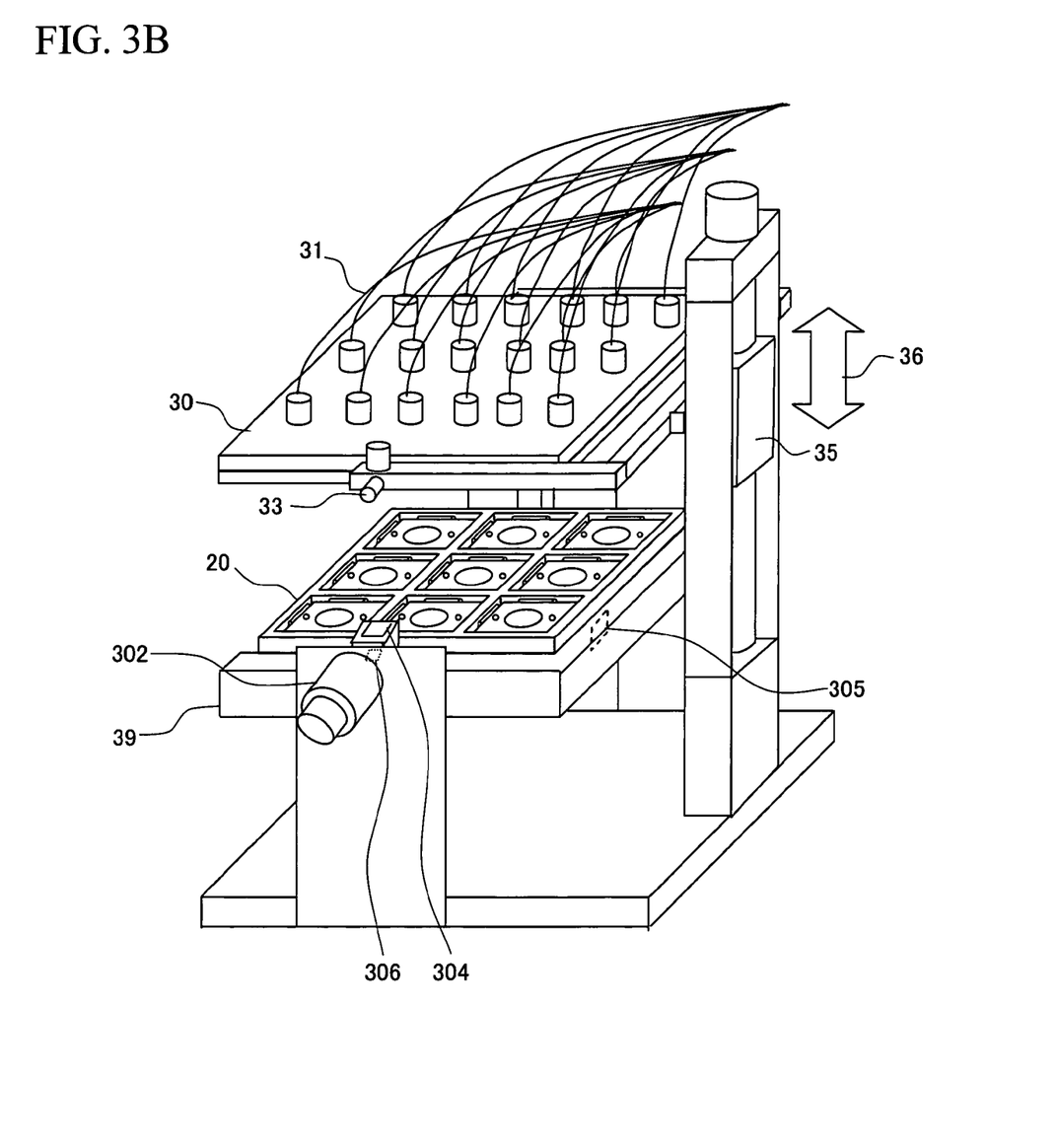
FIG. 3B is a conceptual diagram (2) relating to connection between the joint connected to the flow passage and the culture vessel set.

When the culture vessel set 20 is inserted into the base 39 as shown in FIG. 3B, a sensor 305 senses presence of the culture vessel set 20. Next, the motor 35 lowers the joint 30 and moves the rotating shaft 33 of the joint 30 to the connection groove 304. When a sensor 306 in the connection groove 304 senses that the rotating shaft 33 is inside the connection groove 304, control is executed (by a motor control portion, not shown) so that the operation of the motor 35 is stopped.

Figure 3C:
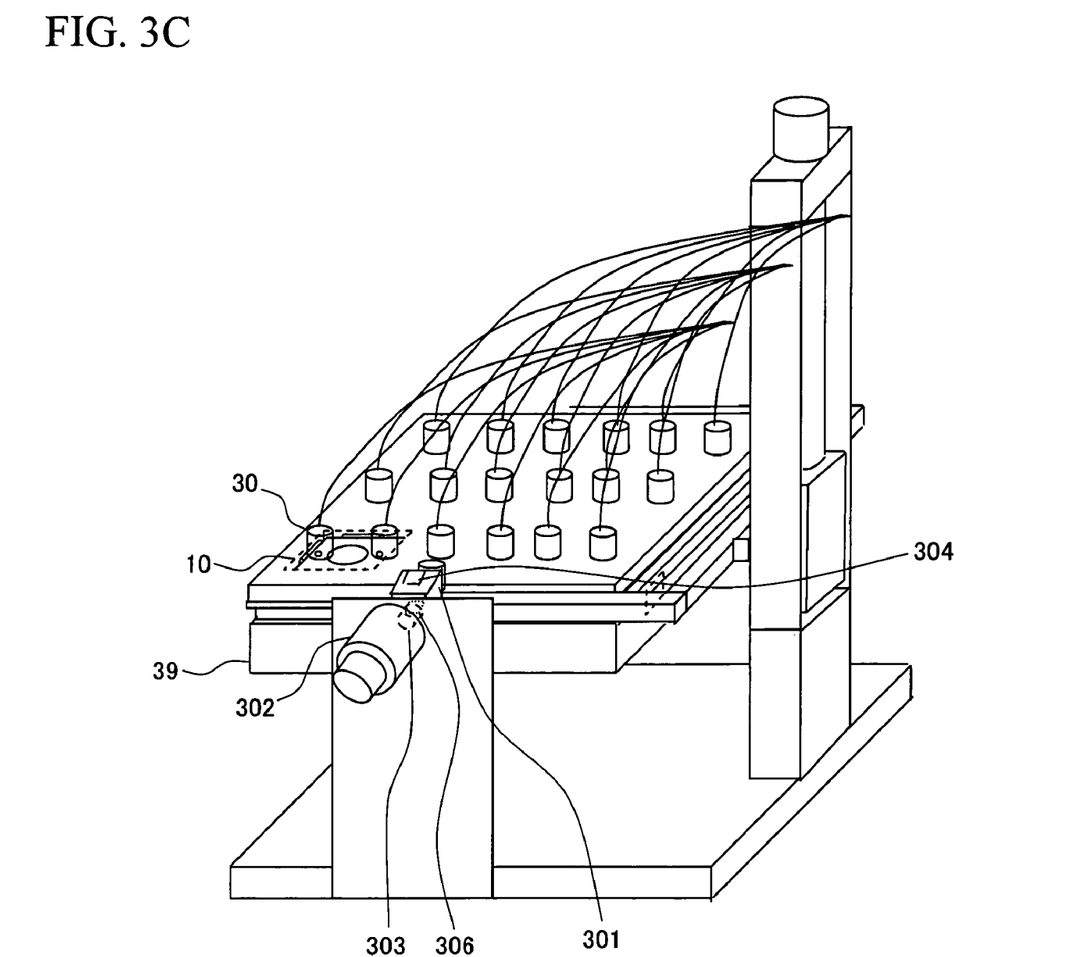
FIG. 3C is a conceptual diagram (3) relating to connection between the joint connected to the flow passage and the culture vessel set.

When the sensor 306 in the connection groove 304 senses the presence of the rotating shaft 33 of the joint 30, the joint 30 and the culture vessel 10 are connected to each other as shown in FIG. 3C, and each rotating shaft (the rotating shaft 33 and the rotating shaft 303) are present on the same line. When the rotating shaft 303 of the motor 302 connected to the arm 301 is rotated (in the arrow 37 direction) in this state, the rotating shaft 33 of the joint 30 is similarly rotated (in the arrow 37 direction), and the culture vessel set 20 on the base 39 and the joint 30 can be rotated (in the arrow 37 direction) in a state connected to each other.

Figure 3D:
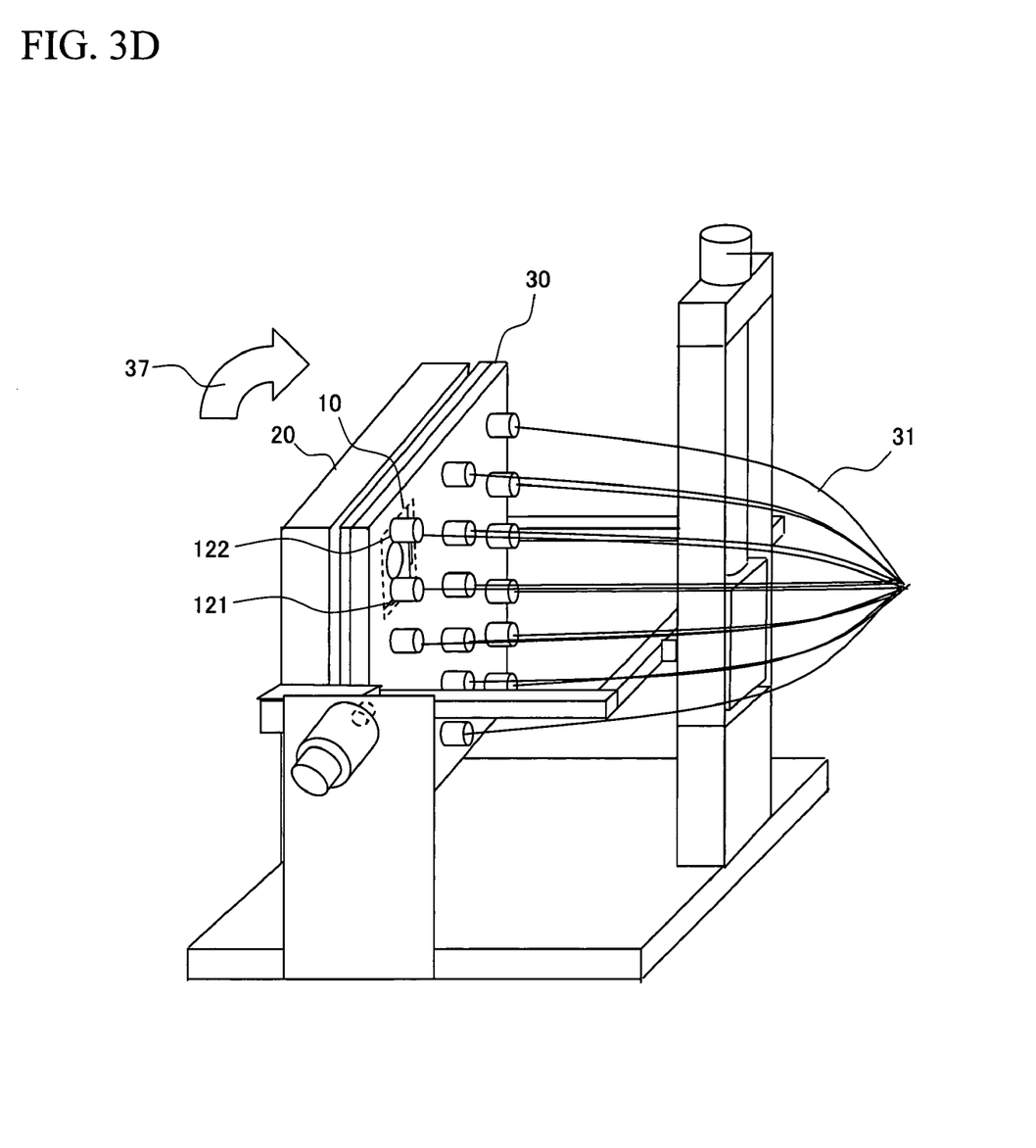
FIG. 3D is a conceptual diagram (4) relating to connection between the joint connected to the flow passage and the culture vessel set.

FIG. 3D shows a state where the joint 30 and the culture vessels 10 are rotated from the horizontal direction to the perpendicular direction (in the arrow 37 direction), and the joint 30 and the culture vessel set 20 are stood in the vertical state. In this state, the (diluted) culture broth flows into the flow passage 31 to be injected into the culture vessel 10. At that time, it is configured such that the culture broth is injected from the liquid injection port 121, which is the lower connection hole 12 of the culture vessel 10, while waste liquid or air flows out of the liquid discharge port 122, which is the upper connection hole 12 of the culture vessel 10 forming the pair.

After the culture vessel has been injected, the state is returned to the horizontal to that in FIG. 3B, the joint 30 is removed from the culture vessel 10 into a completely separated state as in FIG. 3A, and replacement of the culture broth or injection of cells in the culture broth is finished.

<Flow-Passage Configuration for Liquid Injection and Discharge>

Next, a flow-passage configuration for injecting the culture broth into the plurality of culture vessels 10 installed in the culture vessel set 20 will be described. First, merits and demerits of each of the most basic types of serial type and parallel type will be described.

(1) In the flow-passage configuration of the serial type, the liquid is put into one single culture vessel 10, its liquid discharge port 122 is connected to the liquid injection port 121 of the subsequent culture vessel 10, and all the culture vessels 10 are connected. This serial-type configuration has a merit that the flow passage and a liquid-feed system is simple, but it has demerits of non-uniformity of the culture broth that the culture broth in the last culture vessel 10 is not fresh at medium displacement, a pressure difference caused by a height when being stood makes control difficult, and contamination by fungi or bacteria of one culture vessel 10 contaminates all.

On the other hand, in the parallel flow-passage configuration, the liquid is injected to all the culture vessels 10 independently in parallel. The parallel-type configuration has merits that even if one culture vessel 10 is contaminated by fungi or bacteria, the other culture vessels 10 are hardly contaminated, the culture broth can be injected uniformly since the culture broth is injected independently, and a pressure difference is not caused at the injection between the culture vessels 10 due to the heights of the culture vessels 10, but this type also has a demerit that the flow passage and the liquid-feeding system might become extremely complicated.

The inventors have conceived a method utilizing the respective merits (this embodiment) based on the examination results. That is, it is the partially parallel-type flow-passage configuration that when the culture vessel set 20 connected to the joint 30 is stood in the vertical direction, the culture vessels 10 aligned in the horizontal direction are connected in parallel and the liquid is fed for each unit.

(2) Referring to FIG. 4, configuration of the partially parallel-type flow passage 31 and the configuration of the joint 30 to be connected to the culture vessel set 20 will be described.

Figure 4:
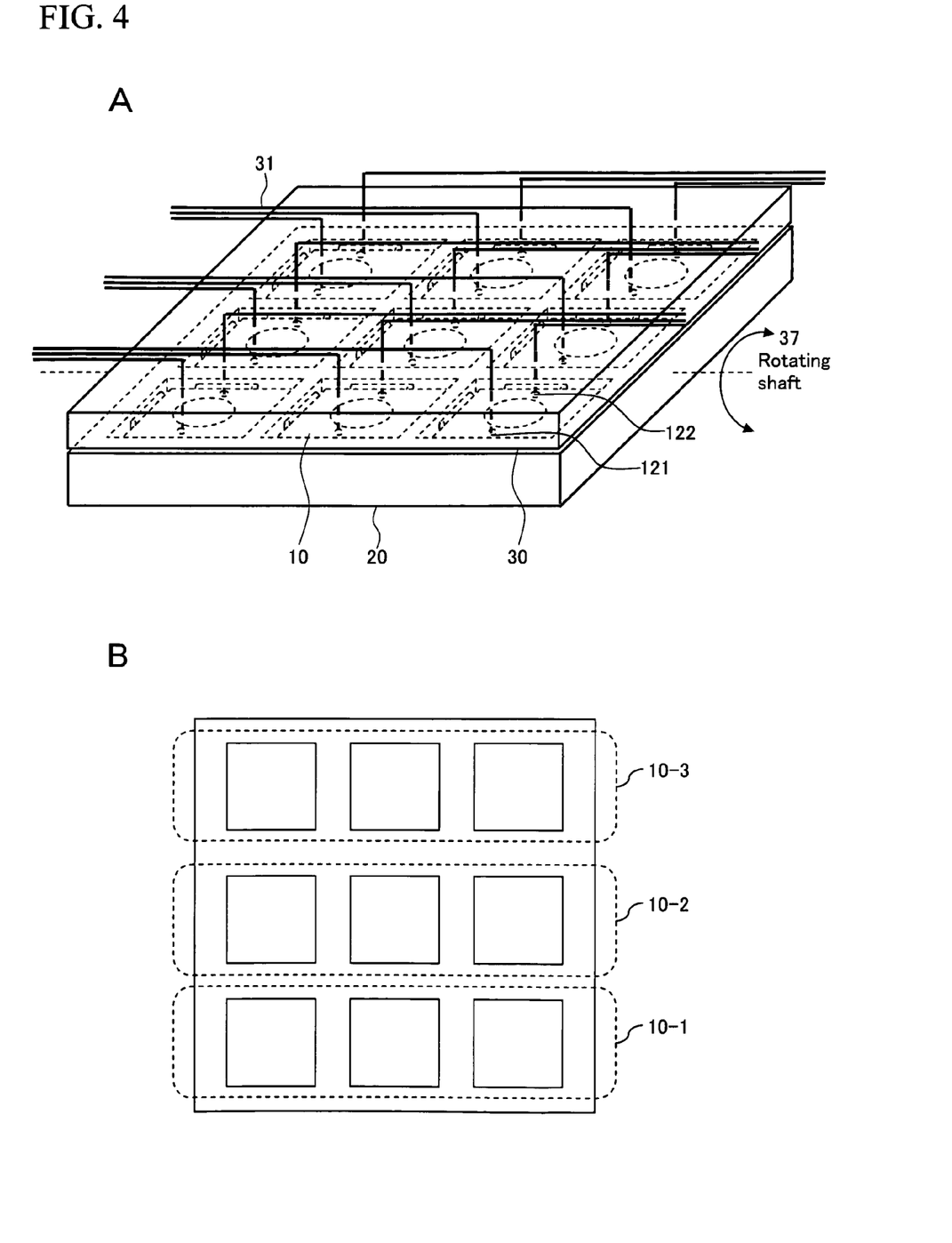
FIG. 4 is a diagram illustrating a conceptual diagram relating to the flow passage (partially parallel type) when the joint and the culture vessel set are connected.

As shown in FIG. 4A, it is configured that when the culture vessel set 20 connected to the joint 30 is rotated in the arrow 37 direction and stood in the vertical direction, parallel treatment can be conducted with the lower connection holes 12 of the culture vessels 10 aligned in the horizontal direction as the liquid injection ports 121 and the upper connection holes 12 as the liquid discharge ports 122. That is, as shown in FIG. 4B, the parallel treatment is conducted by the unit of each group of 10-1, 10-2, 10-3.

By additionally arranging the plurality of culture vessels 10 aligned horizontally in the perpendicular direction in the state where the culture vessel set 20 is stood upright, the merit of the serial type can be obtained that the flow passage and the liquid-feeding system are simplified and the merit of the parallel type such as difficulty in contamination of the whole, uniform injection of the culture broth, no pressure difference by the heights of the culture vessels 10 and the like can be both obtained in the configuration.

<Operation of Parallel-Type Liquid-Feeding/Liquid-Discharge System>

Returning to FIG. 1, a flow of the culture broth in the liquid injection/discharge system having an entire flow passage to realize the partially parallel flow passage 31 will be described.

The culture broth 15 with cell is inputted from the outer door 161 of the air-lock chamber 16 installed at the cell culture device 1 and enters the air-lock chamber 16. Then, the inner door 162 of the air-lock chamber 16 is opened, a flow-passage manipulator 163 is lowered by motor driving from there, and the culture broth 15 with cell is sucked by the pump 17 and moved to the tank 19. Also, the culture broth 181 for dilution is moved to the tank 19 by the pump 17 and density of the cell is adjusted. At that time, the culture broth 192 in the tank 19 is monitored by a tank liquid level sensor 191. Here, at medium replacement, the liquid-feeding process of the culture broth 15 for cell is not required, but only the culture broth 181 for dilution is moved to the tank 19.

And the diluted culture broth 192 is fed by the pump 17 to the multi-way valve 40 from the tank 19. After that, the diluted culture broth 192 is branched by the multi-way valve 40 made of an electromagnetic valve 41, and the diluted culture broth 192 is fed into the culture vessel 10. Here, the liquid is fed only to the culture vessels 10 (culture vessel group 10-1) having a height $y1$ in the perpendicular direction to the liquid injection port 121 of the culture vessel 10 from the multi-way valve 40 at the same time. The liquid is similarly fed to $y1+y2$ (culture vessel group 10-2), $y1+y2+y3$ (culture vessel group 10-3) in FIG. 1. Here, diameters of the tube 42 and a connector 43 used by each group are set the same so that a difference by pressure is not caused other than the height. In the same group, since the liquid-injection positions and the liquid discharge positions (height) are set the same, it is configured such that a pressure difference is not caused at the liquid injection and the liquid discharge.

The extra culture broth coming out of the liquid discharge port 122 of the culture vessel 10 is sensed by the liquid level sensor 104 as the used culture broth 25. On the basis of the sensing result, the controller 106 closes the tube 42 by a pinch-valve like electromagnetic valve 105. Thereby, the diluted culture broth 192 can be easily put into the other culture vessels 10 to which the liquid is fed at the same time. Here, when the electromagnetic valve 105 of the same liquid-feeding system is closed (when the extra culture broth comes out of the liquid discharge ports of all the culture vessels in the same group and the electromagnetic valve 105 is closed), the electromagnetic valve 41 of the multi-way valve 40 is switched to another valve and the liquid is fed to the culture vessels 10 with another height (another culture vessel group). At that time, if all the electromagnetic valves 105 of the same liquid-feeding system are not closed but such an amount of the culture broth 192 that can fill all the culture vessels 10 in the culture vessel group is being fed, an error is displayed as liquid leakage. When the electromagnetic valves. 105 of all the culture vessel groups are closed, it is considered as work finished, the joint 30 and the culture vessel set 20 are removed, and the culture is continued. The waste liquid remaining in the flow passage 31 is all moved to the waste container 24.

<Configuration of Multi-Way Valve>

Using FIGS. 5 to 7, configuration of the multi-way valve 40 will be described. The multi-way valve 40 in this embodiment has one port of inlet and nine ports of outlet. The culture vessel set 20 is configured such that laterally three vessels and vertically three vessels, totaling in nine culture vessels 10 can be set. In the multi-way valve 40, the number of ports can be increased to 20 at the maximum.

Figure 5:
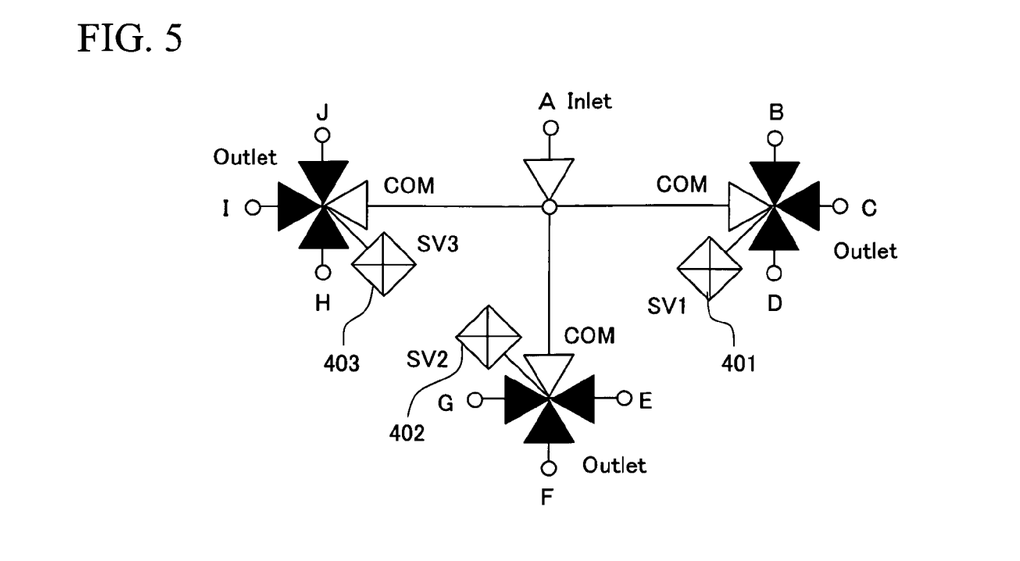
FIG. 5 is a flow-passage configuration diagram of multi-way valve in order to realize the flow passage.

FIG. 5 shows a fluid circuit. When the culture vessel set 20 is stood in the vertical direction (See FIG. 3D), since the number of culture vessels included in the same culture vessel group in the horizontal direction is 3, in the multi-way valve 40, one electromagnetic valve 41 has parallel three ports and since there are three rows in the perpendicular direction, three sets of the electromagnetic valves 41 having the parallel three ports are provided, totaling in nine ports. At a port number A, the culture broth 192 is put into the multi-way valve 40, while port numbers B, C, and D are parallel at an electromagnetic valve SV1 (401), port numbers E, F, and G at an electromagnetic valve SV2 (402), and port numbers H, I, and J at an electromagnetic valve SV3 (403) so that the culture broth 192 can be discharged in parallel.

Figure 6:
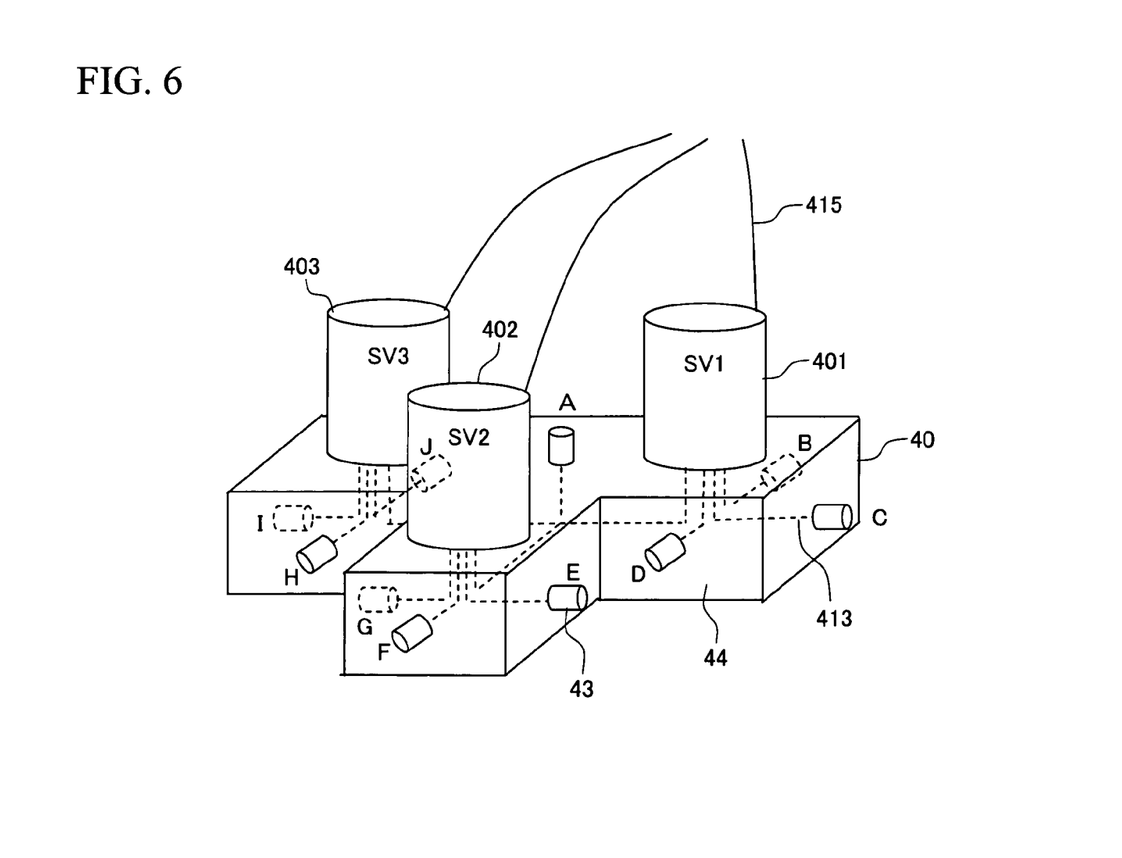
FIG. 6 is an entire configuration diagram of the multi-way valve in the flow passage.
Figure 7:
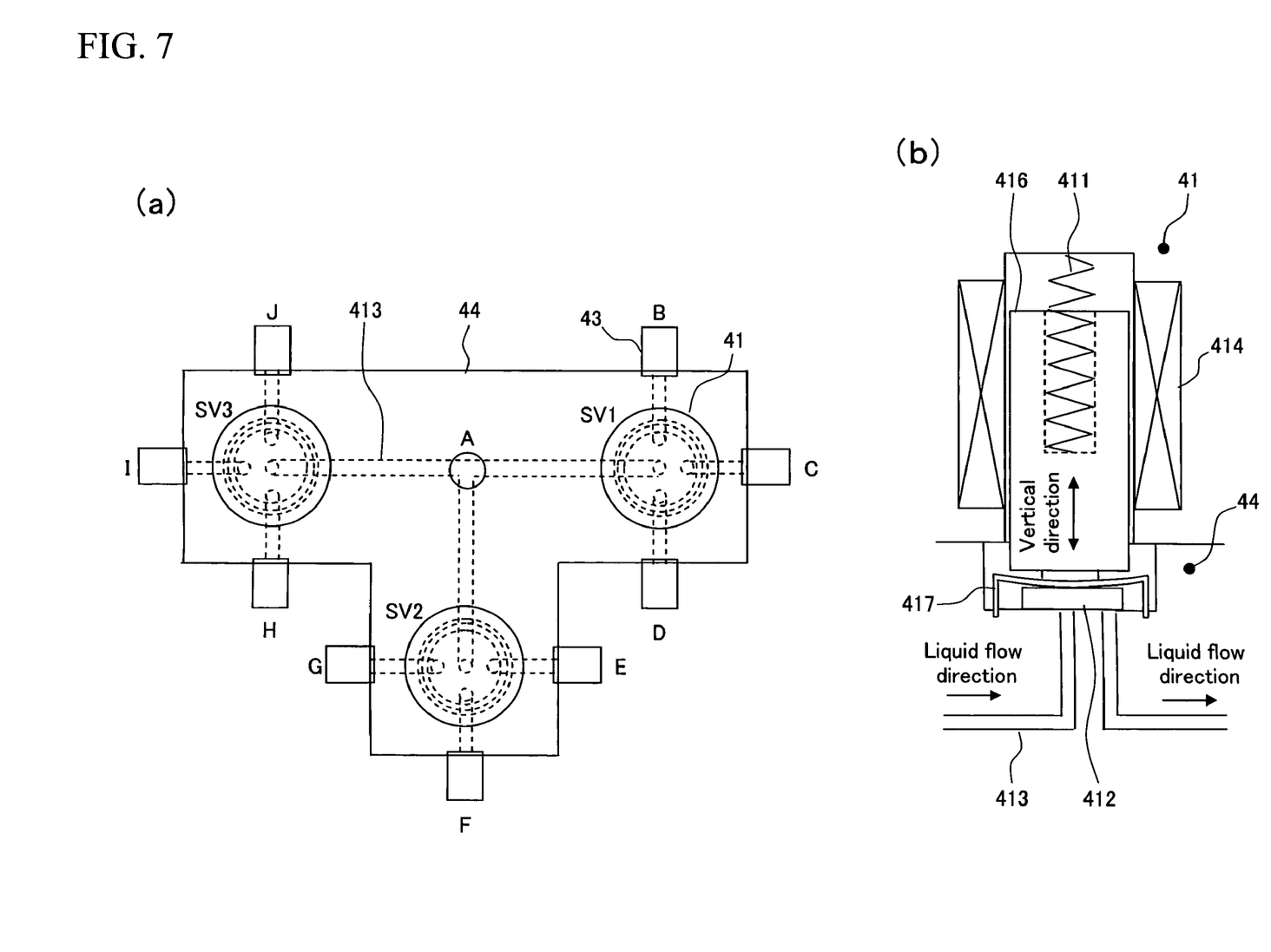
FIG. 7 is a detailed configuration diagram of a flow passage and a valve portion inside the multi-way valve.

FIG. 6 is a view illustrating arrangement and configuration of each port and each electromagnetic valve 41 in a three-dimensional manner. FIG. 7A is a top view of the multi-way valve 40, and FIG. 7B is a view illustrating inner configuration of each electromagnetic valve 41.

The multi-way valve 40 is constituted by a manifold 44 having a flow passage 413 and the electromagnetic valve 41 of a diaphragm type 417. This electromagnetic valve 41 is in a normally closed (NC) state where a plug 412 is pressed by a spring 411 onto the flow passage 413, but when electricity from a wire 415 flows through a solenoid 414 so as to form a magnetic field, a permanent magnet 416 is lifted and the plug 412 is removed, by which the flow passage 413 is opened. When the electricity is stopped, the permanent magnet 416 is lowered by the spring 411 and the plug 412 is placed. The tube 42 from the outside and the manifold 44 are connected to each other by the connector 43. The culture broth 192 from the tank 19 first enters the manifold 44 through A, but since all the electromagnetic valves 41 are closed, the liquid does not flow. When the electricity flows from the controller and the electromagnetic valve SV1 (401) is opened, for example, equal amounts of the culture broth 192 flow from the connectors B, C, and D. Here, in order to eliminate the pressure difference caused by a difference in the heights, the heights from the manifold 44 bottom face to the connector 43 are all equal.

<Software Realization of Liquid-Feeding Operation>

Figure 8:
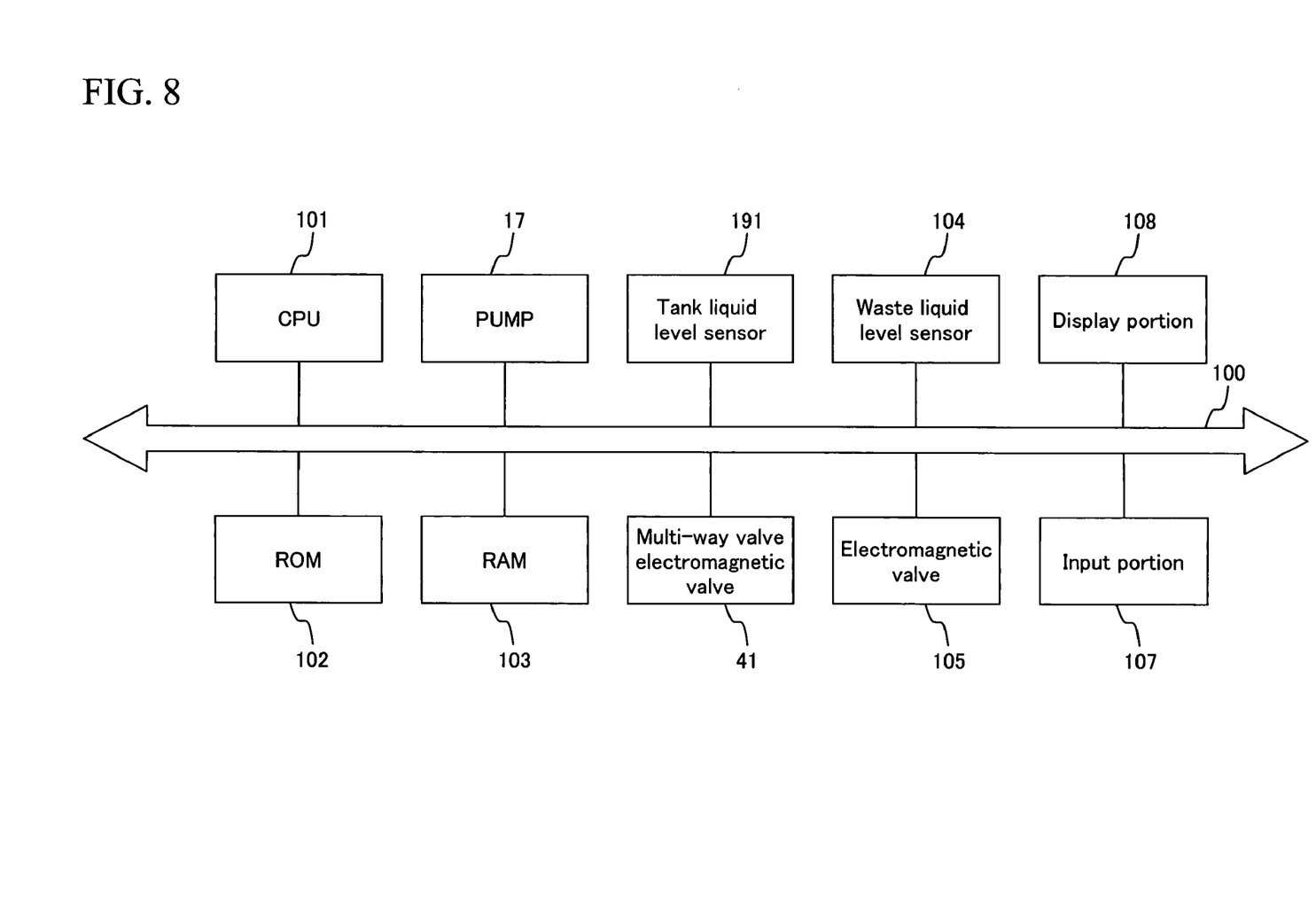
FIG. 8 is a diagram illustrating block configuration of a liquid-feeding system according to the embodiment of the present invention.
Figure 9:
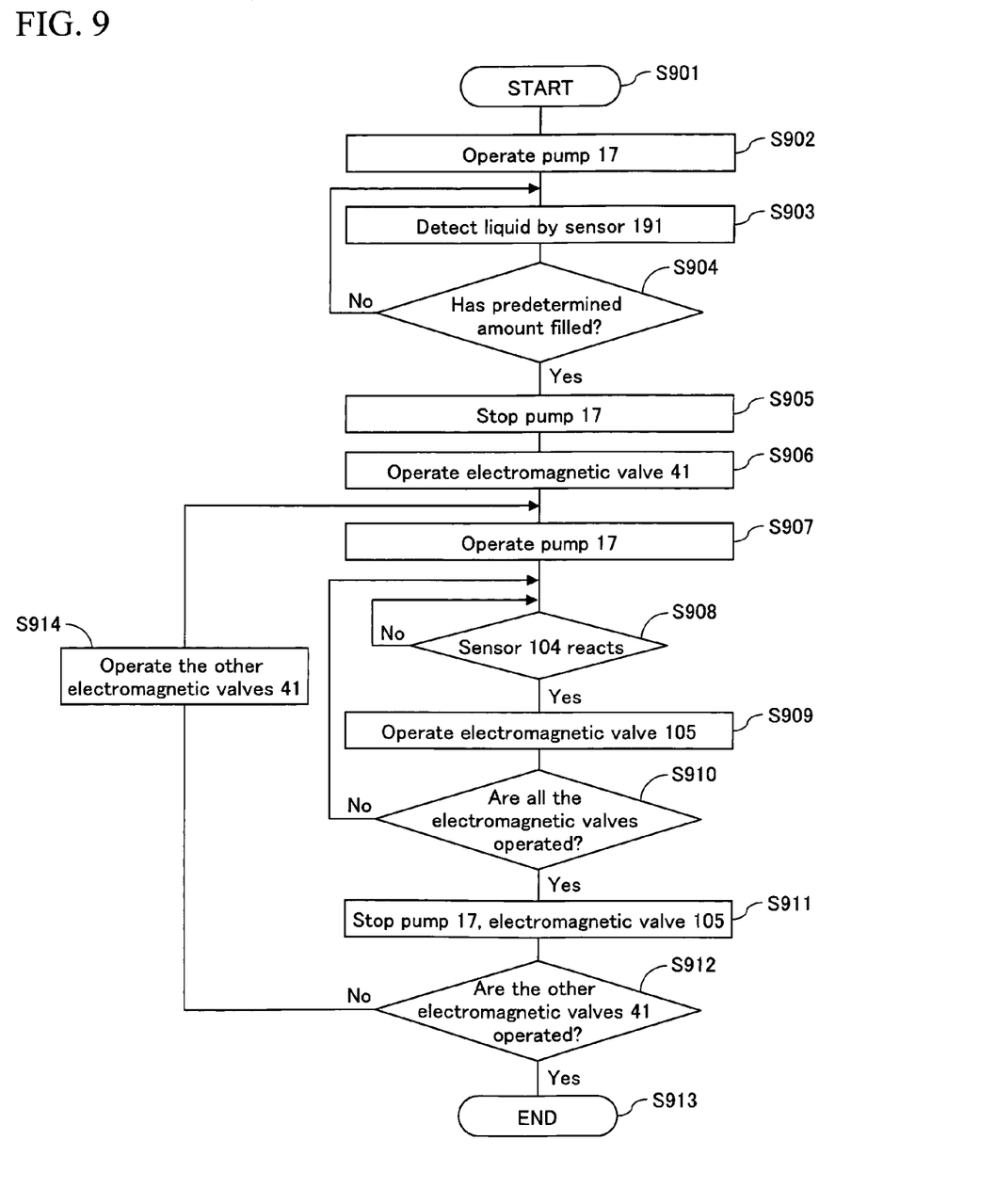
FIG. 9 is a flowchart for explaining an operation of the liquid-feeding system according to the embodiment of the present invention.

In the present invention, the above-described liquid-feeding operation can be realized using a computer program. FIG. 8 is a block diagram illustrating configuration of a portion relating to computer control in the entire liquid-feeding system by the embodiment of the present invention. Each block in FIG. 8 is connected by a bus 100. FIG. 9 is a flowchart for explaining the operation of the liquid-feeding system.

(1) In FIG. 8, a CPU 101 controls the entire operation of the liquid-feeding system and constitutes at least a control entity of the operation by the flowchart shown in FIG. 9. That is, the CPU 101 reads out a control program based on the flowchart in FIG. 9 stored in a ROM 102 upon operation start of the system, extends it on a RAM 103 and controls the entire system. It is possible that the operation of the controller 106 is executed by the CPU 101.

The pump 17 is used for moving the culture broth in the flow passage. The pump 17 is operated forward or backward or its speed can be changed by the CPU 101. The tank liquid level sensor 191 senses that a liquid is filled in the tank 19 with light in a band not damaging a cell and the like and transmits a signal to a control portion. The waste liquid level sensor 104 is connected to the tube 42 so as to sense if the liquid is filled in the tube 42 and transmit a signal to the controller 106. The sensor is different depending on whether it is for cell seeding without culture broth in the culture vessel 10 in the beginning or it is for medium replacement with the culture broth in the beginning. In the multi-way valve electromagnetic valve 41 and the electromagnetic valve 105, the valves are opened/closed by flowing electricity to the solenoid upon the signal from the respective sensors.

An input portion 107 is for a user to instruct carrying-in/-out of the culture vessel, for example, and corresponds to a keyboard, a mouse and the like. A display portion 108 displays that the culture system is in operation, instruction contents from the user and the like and corresponds to a CRT, a liquid crystal display and the like.

(2) Subsequently, the operation of the liquid-feeding system provided with the configuration as in FIG. 8 will be described using FIG. 9. Here, the medium replacement mainly operating in the liquid-feeding system will be described. The culture broth 15 containing cell is fed to the tank 19 by the pump 17 before this process. Unless otherwise specified, the operation entity is the CPU 101.

When the medium replacement is required (Step S901), the pump 17 is operated so as to feed the culture broth 181 to the tank 19 (Step S902). The sensor 191 senses that the culture broth 181 is filled in the tank 19 (Step S903), and an amount of the culture broth 192 is determined (Step S904). When a predetermined amount of the culture broth 192 is filled, processing moves to Step S905, and if the culture broth 192 is not completely filled, the routine returns to Step S903, and the pump 17 is continuously operated. Here, the liquid level of the culture broth 192 is detected by the liquid level sensor 191, and a detection result is transmitted to the CPU 101.

If it is determined at Step S904 that the entire culture broth 192 is filled, the operation of the pump 17 is stopped (Step S905). Electricity is flown to the electromagnetic valve 41 of the multi-way valve 40 required for liquid-feeding so as to open the flow passage 413 (Step S906) and to operate the pump 17, and the culture broth 192 in the tank 19 is fed into the culture vessel 10 (Step S907). Connection between the culture vessel set 20 and the joint 30 has been completed so far, and the culture vessel set 20 is in a standing state as in FIG. 3D.

The culture broth 192 is filled in the culture space 11 inside the culture vessel 10, the extra culture broth or the used culture broth 25 comes out of the liquid discharge port 122 through the tube 42, and if the waste liquid sensor 104 senses that (Step S908), electricity is made to flow to the electromagnetic valve 105 in the tube 42 (Step S909), and discharge of the extra culture broth is stopped by closing the flow passage 413. In the culture vessel 10 placed in parallel (the same culture vessel group), upon sensing by the waste liquid sensor 104 of the tube 42 coming out of the liquid discharge port 122, if electricity does not flow through the electromagnetic valve 105, the routine returns to Step S908, and the pump 17 is continuously operated so as to continue flowing the diluted culture broth 192. However, even if all the electromagnetic valves 105 are not operated after an amount that can be replaced by the entire diluted culture broth 192 is flown, it is considered to be caused by liquid leakage or a failure in the device, and an error code is displayed on the display portion. If it is determined at Step S910 that all the electromagnetic valves 105 are being operated, the routine goes on to Step S911, the pump 17 is stopped, and the electromagnetic valve 41 of the multi-way valve 40 is closed (Step S911). If all the electromagnetic valves 41 of the multi-way valve 40 are not operated, the electromagnetic valve 41 not in operation is opened (Step S914), and the routine goes to Step S907. If it is determined at Step S912 that all the electromagnetic valves 41 are being operated, the routine goes on to Step S913, and the liquid-feeding work is finished.

The function of the embodiment can be also realized by a program code of the realizing software. In this case, a recording medium in which the program code is recorded is provided to the system or the device, and the system or a computer of the device (or CPU or MPU) reads out the program code stored in the recording medium. In this case, the program code itself read out of the recording medium realizes the above-mentioned function of the embodiment, and the program code itself and the recording medium storing it constitute the present invention. The recording mediums providing the program code include a floppy (registered trademark) disk, CD-ROM, DVD-ROM, hard disk, optical disk, magnetooptical disk, CD-R, magnetic tape, non-volatile memory card, ROM and the like.

Also, on the basis of an instruction of the program code, OS (operating system) operating on the computer may execute a part of or the whole of the actual processing so that the above-mentioned function of the embodiment is realized by the processing. Moreover, after the program code read out of the recording medium is written in a memory on the computer, on the basis of the instruction of the program code, a part of or the whole of the actual processing may be executed by a CPU of the computer and the like so that the above-mentioned function of the embodiment is realized by the processing.

Also, it may be so configured that a program code of the software that realizes the function of the embodiment is delivered through a network, the code is stored in storage means such as a hard disk of the system or the device, a memory and the like or a recording medium such as CD-RW, CD-R and the like and the computer (or CPU or MPU) of the system or the device reads out and executes the program code stored in the storage means or the recording medium.

<Conclusion>

In the flow-passage structure by the embodiment of the present invention, a single electromagnetic valve is allocated to all the culture vessels at an equal height in the horizontal direction, and an equal amount of a liquid is fed at the same time by controlling ON/OFF of the electromagnetic valve. Thereby, the liquid can be fed to the plurality of cartridges at the same time. Thus, efficiency of the entire flow-passage system and reduction of the liquid-feeding time can be promoted, by which damage applied to a cell such as an external force by a temperature and water pressure can be minimized.

Here, the culture vessels to which the liquid is fed at the same time and the outlet from the electromagnetic valve are set at the equal height in the horizontal direction because a difference in a medium injection amount caused by water head difference by the height at the height of the culture vessel according to Pascal's principle is to be eliminated. At this time, a diameter and a length of a flow passage from the electromagnetic valve to the culture vessel are supposed to be all the same. Thereby, a pressure to each culture vessel at the liquid-feeding can be made equal.

Also, the culture vessel and the joint can be detached. Thus, the inside of the flow passage can be made washable so that clogging in the flow passage caused by solidification of protein and the like can be eliminated.

Moreover, if the culture vessel and the joint are not connected, it is a closed-system culture vessel, while if the culture vessel and the joint are connected, the flow passage is made through. Thus, bacteria or fungus does not intrude but the liquid can be fed in a clean state.

Alternatively, a sensor may be provided in the flow passage after the liquid-feeding so that the flow passage is blocked by an electromagnetic valve on the outlet side on the basis of a detection result of the sensor. Thereby, a required amount of medium can be reduced, and efficiency can be improved.

Though not described in the embodiment, in the present invention, the shapes of the culture vessel set and the joint can be changed. Thereby, it is possible to respond to various shapes of the culture vessels or one or plural culture vessels. Therefore, even if a culture vessel is different depending on a tissue to be cultured, the system can be used, and an extremely flexible cell culture system can be constructed.

The present invention can respond to various culture conditions by the culture vessel set or the multi-way electromagnetic valve to one or plural culture vessels as mentioned above or moreover, only by changing the shapes of the joint and the culture vessel set. Thereby, in the automation of the cell culture work requiring high cleanliness realized by an unattended room, general-purpose properties can be provided, numerous culture vessels can be coped with, and medium can be injected with high efficiency and uniformity, and thus, demand is high in the industries including cell transplantation and regeneration medicine and availability is expected to be high.

What is claimed is:

1. A cell culture device for culturing a cell using a culture vessel, comprising:
 a culture vessel set having a culture vessel holder adapted to hold a plurality of culture vessels, wherein the culture vessel holder is provided with plural culture vessel holding parts which are arranged in m rows and n columns, the culture vessel set having a first position and a second position;

a culture set holding part holding the culture vessel set;

a state changing part connecting with the culture set holding part to change a state of the culture vessel set from the first position to the second position;

a plurality of valve members located in each column of the culture vessel holder, respectively, each valve members configured to control liquid injection and liquid discharge of the culture vessel through each partially parallel-type flow passage;

a plurality of partially parallel-type flow passages which are connected with the plurality of culture vessel holding parts in a first one of the m rows, respectively; and a controller for controlling the state changing part and the plurality of valve members, wherein, when the culture vessel set is changed from the first position to the second position, the controller controls the valve member corresponding to a first column of the culture vessel holder so as to perform the liquid injection or discharge for the plurality of culture vessel holding parts in the first one of the m rows, and wherein after performing the liquid injection or discharge for the plurality of culture vessel holding parts in the first one of the m rows, the controller controls the valve member corresponding to a second column of the culture vessel holder so as to perform the liquid injection or discharge for the plurality of culture vessel holding parts in the second one of the m rows.

2. The cell culture device according to claim 1, further comprising:

a sensor for detecting an amount of liquid discharged from the plurality of culture vessel holding parts in the first one of the m rows, wherein the controller controls a switching operation of the valve member in response to information from the sensor.

3. The cell culture device according to claim 1, wherein each partially parallel-type flow passage has tubes connected with the plurality of culture vessel holding parts in the first one of the m rows, and each of the tubes have a same diameter.

4. The cell culture device of claim 1, wherein the first position is a horizontal position and the second position is a vertical position.

5. The cell culture device of claim 4, wherein, in the vertical position, the plurality of culture vessel holding parts in the first one of the m rows are located at the same height.

6. The cell culture device of claim 1, wherein, the valve member is an electromagnetic valve.

* * * * *